United States Patent
Bogert et al.

(10) Patent No.: US 9,724,660 B2
(45) Date of Patent: Aug. 8, 2017

(54) TELESCOPING PLUNGER ASSEMBLY

(71) Applicant: GLOBUS MEDICAL, INC., Audubon, PA (US)

(72) Inventors: Roy B. Bogert, Lincoln Park, NJ (US); James W. Nelson, Morristown, NJ (US)

(73) Assignee: Globus Medical, Inc., Audubon, PA (US)

( * ) Notice: Subject to any disclaimer, the term of this patent is extended or adjusted under 35 U.S.C. 154(b) by 58 days.

(21) Appl. No.: 14/754,761

(22) Filed: Jun. 30, 2015

(65) Prior Publication Data

US 2015/0298080 A1    Oct. 22, 2015

Related U.S. Application Data

(63) Continuation of application No. 13/549,925, filed on Jul. 16, 2012, now Pat. No. 9,144,446, which is a continuation of application No. 12/492,870, filed on Jun. 26, 2009, now abandoned, which is a continuation of application No. 11/322,067, filed on Dec. 28, 2005, now abandoned.

(60) Provisional application No. 60/691,859, filed on Jun. 17, 2005.

(51) Int. Cl.
| | |
|---|---|
| *A61B 17/56* | (2006.01) |
| *B01F 13/00* | (2006.01) |
| *A61B 17/88* | (2006.01) |
| *B01F 15/02* | (2006.01) |
| *B01F 15/00* | (2006.01) |
| *A61F 2/30* | (2006.01) |
| *B01F 7/00* | (2006.01) |

(52) U.S. Cl.
CPC ...... *B01F 13/0023* (2013.01); *A61B 17/8822* (2013.01); *B01F 7/00416* (2013.01); *B01F 13/002* (2013.01); *B01F 15/00506* (2013.01); *B01F 15/027* (2013.01); *B01F 15/0278* (2013.01); *A61F 2002/30405* (2013.01); *A61F 2002/30601* (2013.01); *A61F 2220/0025* (2013.01); *B01F 7/0025* (2013.01); *B01F 2215/0029* (2013.01)

(58) Field of Classification Search
CPC ............ A61B 17/8802; A61B 17/8811; A61B 17/8833; A61B 2017/8838; A61B 17/8822
USPC ........... 606/92–95; 604/82–92; 366/130–144
See application file for complete search history.

(56) References Cited

U.S. PATENT DOCUMENTS

| 5,728,075 A | 3/1998 | Levander |
| 6,024,480 A * | 2/2000 | Seaton ............... A61B 17/8822 206/222 |
| 6,033,105 A * | 3/2000 | Barker ............... A61B 17/8816 222/241 |
| 7,371,241 B2 | 5/2008 | Evans et al. |
| 8,702,795 B2 | 4/2014 | Shoji et al. |
| 2002/0191487 A1 * | 12/2002 | Sand ..................... B01F 7/0005 366/252 |

(Continued)

*Primary Examiner* — Matthew Lawson (57) ABSTRACT

A bone filler mixing and delivery device includes a mixing section adapted to mix components to form bone filler. A syringe barrel is coupled to the mixing section and has an opening through which the bone filler can be dispensed. A controllable portal can be manipulated to open a flow path between the mixing section and the syringe barrel. A plunger assembly is adapted to extend telescopically in an axial direction through the syringe barrel to dispense the bone filler through the opening.

19 Claims, 12 Drawing Sheets

(56) References Cited

U.S. PATENT DOCUMENTS

| | | |
|---|---|---|
| 2003/0012079 A1 | 1/2003 | Coffeen et al. |
| 2004/0066706 A1 | 4/2004 | Barker et al. |
| 2004/0196735 A1* | 10/2004 | Barker ............... A61B 17/8833 366/139 |
| 2008/0039855 A1* | 2/2008 | Lambert ............ A61B 17/8822 606/93 |

\* cited by examiner

TELESCOPING PLUNGER ASSEMBLY

CROSS-REFERENCE TO RELATED APPLICATIONS

This application is a continuation of U.S. application Ser. No. 13/549,925, filed on Jul. 16, 2012, which is a continuation of U.S. application Ser. No. 12/492,870, filed Jun. 26, 2009, abandoned, which is a continuation of U.S. application Ser. No. 11/322,067, filed Dec. 28, 2005, abandoned, which claims the benefit of priority of U.S. Provisional Patent Application No. 60/691,859, filed Jun. 17, 2005, the contents of which are incorporated herein by reference in their entireties for all purposes.

TECHNICAL FIELD

The present application relates to plunger assemblies and, more particularly, to telescoping plunger assemblies.

BACKGROUND

Syringe assemblies have been used to deliver bone filler to patients. Typically, syringe assemblies include a syringe barrel with an opening at one end for delivering the bone filler. A plunger assembly is usually adapted to pass through the syringe barrel and push the bone filler through that opening.

In order to deliver a greater amount of bone filler, from a syringe assembly, typically, a larger syringe barrel is provided (i.e., a barrel that is larger in diameter and/or longer),

SUMMARY OF THE INVENTION

The present disclosure relates to telescoping plunger assemblies for a material delivery device. The material delivery device typically includes a first compartment to temporarily store the material and a syringe barrel coupled to the first compartment. A plunger assembly is adapted to extend telescopically from a compacted state substantially contained within a first compartment of the device through the syringe barrel to dispense material.

In some implementations, the material delivery device is a bone filler mixing and delivery device. Examples of bone cement mixing and delivery devices are disclosed in U.S. patent application Ser. Nos. 10/438,471, 10/637,908 and Ser. No. 11/252,515, which are incorporated by reference. A person of ordinary skill would understand that the techniques and devices disclosed herein could be readily adapted to any type of material delivery device.

In one aspect, a bone filler mixing and delivery device includes a mixing section with a mixing element adapted to mix components to form bone filler. A syringe barrel is coupled to the mixing section and has an opening through which the bone filler can be dispensed. A controllable portal (also referred to as an access portal) is provided that can be manipulated to open a flow path between the mixing section and the syringe barrel. A plunger assembly is adapted to extend telescopically in an axial direction through the syringe barrel to dispense the bone filler through the opening. In certain implementations, the plunger assembly is adapted to telescopically retract to a position completely contained within the mixing section.

In some implementations, the telescoping plunger assembly includes a drive shaft that can be rotated about an axis, a lead screw threaded to the drive shaft and a plunger shaft threaded to the lead screw. Typically, in those implementations, the drive shaft is restricted from moving in an axial direction and the plunger shaft is restricted from moving in a rotational direction.

According to some implementations, rotation of the drive shaft causes relative rotation between the lead screw and at least one of either the plunger shaft or the drive shaft. Typically, in those implementations, the relative rotation causes the plunger shaft to move axially through the bone filler mixing and delivery device.

Certain implementations include a support sleeve adapted to provide mechanical support to the plunger shaft. In those implementations, the plunger shaft can be coupled to the support sleeve in a manner that allows relative motion between the plunger shaft and the support sleeve in an axial direction, but restricts relative motion between the plunger shaft and the support sleeve in a rotational direction. In some implementations, a longitudinal slot is formed in the plunger shaft and a pin extends from the support sleeve to engage the longitudinal slot and prevent the plunger shaft from rotating about the axis. The pin may be adapted to move longitudinally through the longitudinal slot as the plunger shaft is moved axially through the bone filler mixing and delivery device.

In another aspect, a material delivery device includes a syringe barrel with a portal for loading material into it and an opening through which the material can be dispensed. A plunger assembly is adapted to extend telescopically through the syringe barrel to dispense the material through the opening. In some implementations, the plunger assembly is adapted to retract telescopically to a position completely outside of the syringe barrel.

In some implementations, the material delivery device has a drive shaft that can be rotated about an axis, a lead screw that is threaded to the drive shaft and a plunger shaft that is threaded to the lead screw. In some of those implementations, the drive shaft is restricted from moving in an axial direction and the plunger shaft is restricted from moving in a rotational direction. In some of those implementations, rotation of the drive shaft causes relative rotation between the lead screw and at least one of either the plunger shaft or the drive shaft, and the relative rotation causes the plunger shaft to move axially through the material delivery device.

According to some implementations, a support sleeve is adapted to provide mechanical support to the plunger shaft. In those implementations, the plunger shaft is coupled to the support sleeve in a manner that allows relative motion between the plunger shaft and the support sleeve in an axial direction, but restricts relative motion between the plunger shaft and the support sleeve in a rotational direction.

In certain implementations, a longitudinal slot formed in the plunger shaft and the material delivery device includes a pin that extends from the support sleeve to engage the longitudinal slot and prevent the plunger shaft from rotating about the axis. In such implementations, the pin is adapted to move longitudinally through the longitudinal slot as the plunger shaft is moved axially through the bone filler mixing and delivery device, Some implementations include a support sleeve that is movable in an axial direction, where the pin is adapted to drag the sleeve in the axial direction with the plunger shaft as the plunger shaft moves beyond an axial position where the pin reaches an end of the longitudinal slot.

Particular implementations include a first section that is coupled to the syringe barrel. In those implementations, the first section is adapted to store the material and the plunger assembly is adapted to extend from the first section through the syringe barrel.

In some implementations, one or more of the following advantages may be present. By implementing a telescoping plunger assembly, material delivery devices, such as a bone filler mixing and delivery devices, may be made more compact than would be otherwise possible. Additionally, such devices might be made easier to handle, which can be particularly important in tight quarters, such as in an operating room.

Other features and advantages will be apparent from the following description, drawings and claims.

BRIEF DESCRIPTION OF THE DRAWINGS

Like reference symbols in the various drawings indicate like elements.

DETAILED DESCRIPTION

The present disclosure relates to a telescoping plunger assembly for a material delivery device. The telescoping plunger assembly includes a syringe barrel with an opening through which material is dispensed and a portal for loading material into the syringe barrel. The plunger assembly is adapted to extend telescopically from a compacted state substantially outside the syringe barrel going through the syringe barrel to dispense material.

In some implementations, the material delivery device is a device adapted to mix and deliver bone filler. Typical bone fillers include bone cement based materials (e.g., polymethyl methacrylate (PMMA)), coral based materials (e.g., Hydroxyapatite), calcium sulfates, beta tricalcium phosphates, silica based materials (e.g., ceramics), and human demineralized bone matrices and polymers, such as biocompatible polylactic-co-glycolic acid (i.e., "plaga").

Figure 1A:
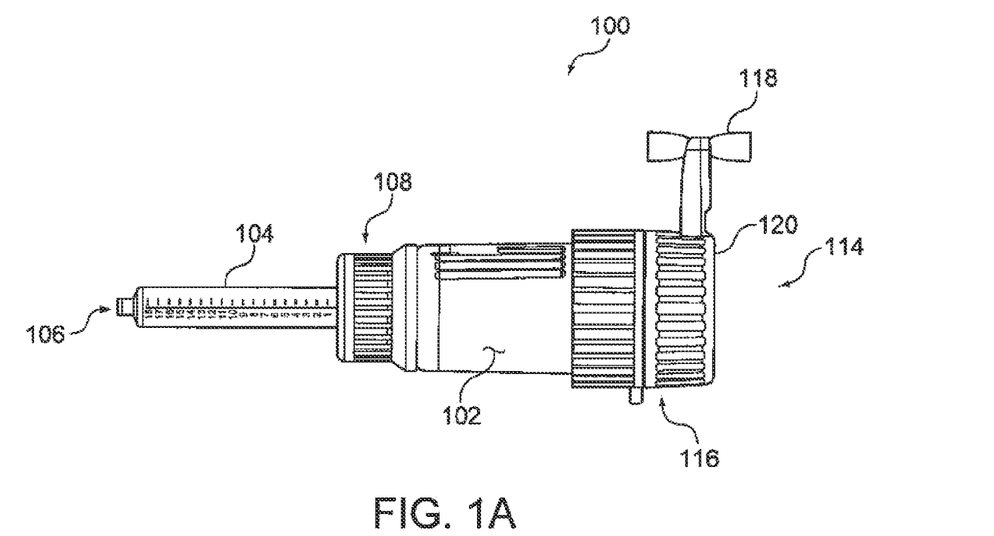
FIGS. 1A and 1B are side views of a bone filler mixing and delivery device.
Figure 1B:
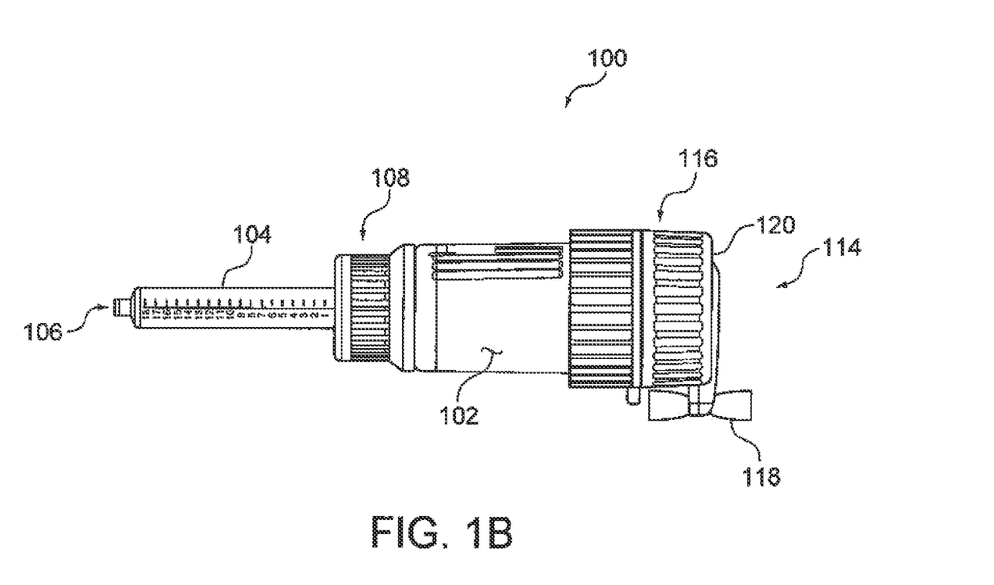

FIGS. 1A and 1B illustrate a bone filler mixing and delivery device 100 that includes a mixing section 102 adapted to mix one or more components to form bone filler. A syringe barrel 104 is coupled to the mixing section 102 and has an opening 106, through which the bone filler can be dispensed. A collar 108 is positioned between the mixing section 102 and the syringe barrel 104 and can be manipulated by a user to actuate a controllable portal that opens a flow path between the mixing section 102 and the syringe barrel 104.

A plunger assembly (not visible in FIG. 1A or 1B) is provided inside the mixing and delivery device 100 and is adapted to extend from a retracted position substantially (or completely) contained within the mixing section 102 in a telescopic manner through the syringe barrel 104 to dispense bone filler through the opening 106 at the end of the syringe barrel 104.

A cover assembly 114 is coupled to the mixing section 102. The cover assembly 114 includes a cap assembly 116 and a crank handle 118. According to the illustrated implementation, the cap assembly 116 is coupled directly to the mixing section housing 102. The crank handle 118 is coupled to the cap assembly 116 with a hinged connection (at 120). The crank handle 118 can be moved about the hinged connection between a first position (shown in FIG. 1A) and a second position (shown in FIG. 1B).

In some implementations, when the crank handle 118 is in the first position (FIG. 1A), it engages mixing paddles inside the mixing chamber, and when the crank handle 118 is in the second position (FIG. 1B), it engages the telescoping plunger assembly. From either the first position or the second position, the crank handle 118 can be rotated about an axis of the device 100 to drive whichever element it is engaged to.

In a typical use of the device 100, bone filler components are introduced into the mixing section 102. With the crank handle in the first position (FIG. 1A), a user rotates the crank handle 118 to mix the bone filler components with the mixing paddles inside the mixing section 102. Once the components are mixed sufficiently, the user opens the controllable portal by manipulating collar 108 to open a flow path between the mixing section 102 and the syringe barrel 104. The mixed bone filler can then pass through the flow path into the syringe barrel 104. The user may continue to drive the mixing paddles until a desired amount of mixed bone filler has been introduced into the syringe barrel 104.

Once a desired amount of bone filler has been introduced into the syringe barrel 104, the user moves the crank handle 118 about the hinged connection to the second position (FIG. 1B). From the second position, the user rotates the crank handle 118 to drive the plunger assembly. The plunger assembly extends in an axial direction from a retracted position substantially contained within the mixing section 102. The extension occurs in a telescopic manner through the syringe barrel 104 to dispense the bone filler through opening 106.

Figure 2:
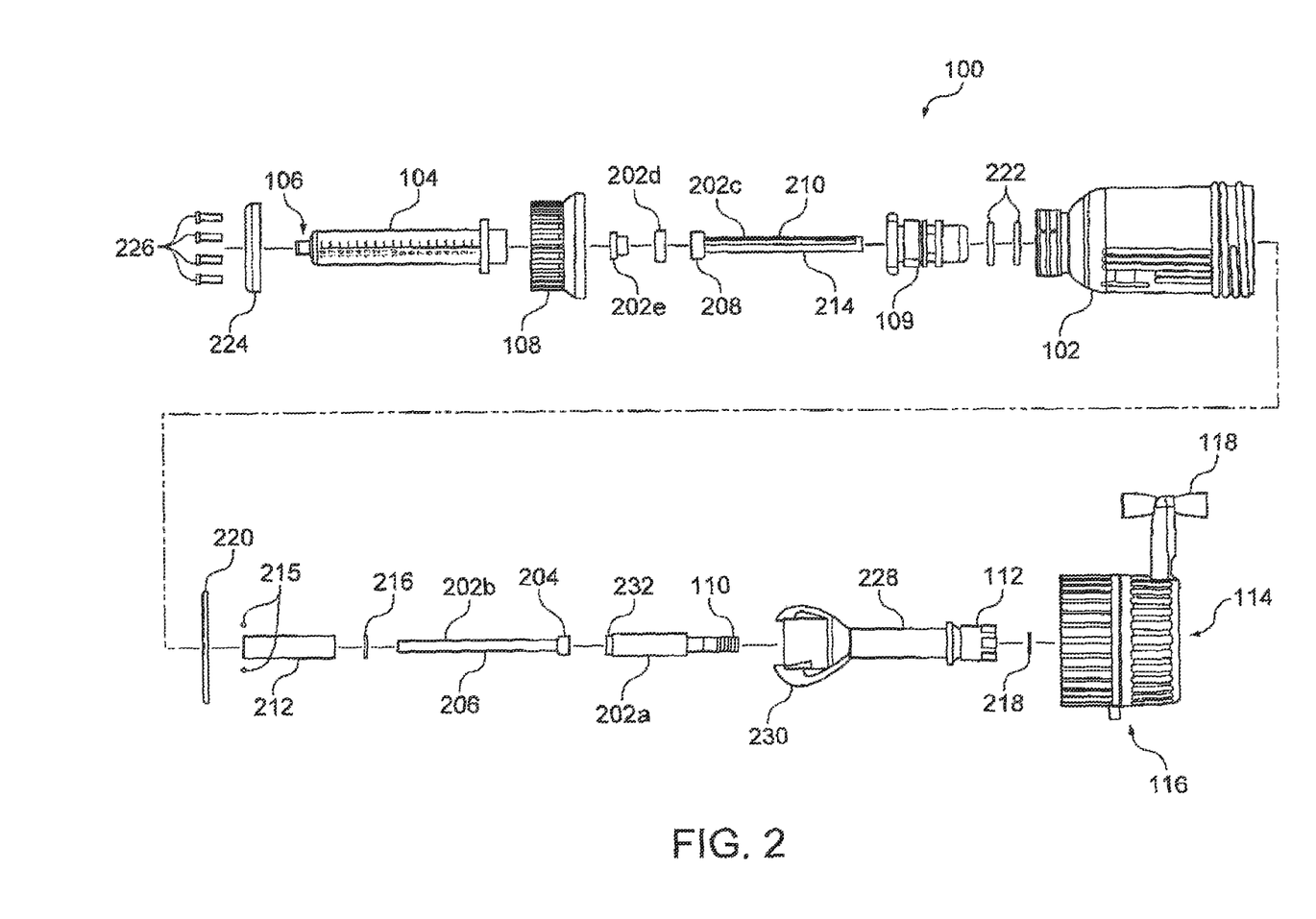
FIG. 2 is an exploded view of a bone filler mixing and delivery device.

FIG. 2 is an exploded view of a bone filler mixing and delivery device 100 with a telescoping plunger assembly. The illustrated device 100 includes a housing 102 for a mixing section (102 in FIGS. 1A-1B). A syringe barrel 104 is adapted to be coupled to mixing section housing 102. The syringe barrel 104 has an opening 106 at a forward end, through which mixed bone filler can be dispensed.

The illustrated device 100 includes a controllable portal that includes a collar 108 that can be manipulated by a user to open a flow path between the mixing section 102 and the syringe barrel 104, and a sliding tube 109 that is adapted to be coupled to the collar 108 so that manipulation of the collar 108 translates into movement of the sliding tube 109.

In some implementations, the sliding tube 109 includes openings that can be aligned with corresponding openings in the mixing section 102 and the syringe barrel 104 to provide a flow path between those areas. In those implementations, manipulating the controllable portal in a particular manner results in the alignment of the sliding tube's 109 opening with the corresponding openings in the mixing section 102 and the syringe barrel 104. Preferably, the sliding tube 109 can form a tight seal with both the mixing section 102 and the syringe tube 104 so that when the flow path is not provided, material cannot accidentally flow from the mixing section 102 to the syringe tube 104. Such sealing may be provided, for example, by o-rings 222.

In some implementations, the controllable portal consists of a collar 108 that is coupled to the sliding tube 109. Such implementations may be adapted so that when the collar 108 is rotated axially, the sliding tube 109 moves in an axial (or other) direction through the device 100 to align one or more ports on the sliding tube with ports elsewhere in the device 100 and thereby open a flow path between the mixing section 102 and the syringe barrel 104.

The illustrated device includes a telescoping plunger assembly. The telescoping plunger assembly includes a drive shaft 202 *a*, a lead screw 202 *b* adapted to be coupled to the drive shaft 202 *a*, a plunger shaft 202 *c* adapted to be coupled to the lead screw 202 *b*, a plunger seal 202 *d* and a seal retaining screw 202 *e*.

Figure 3A:
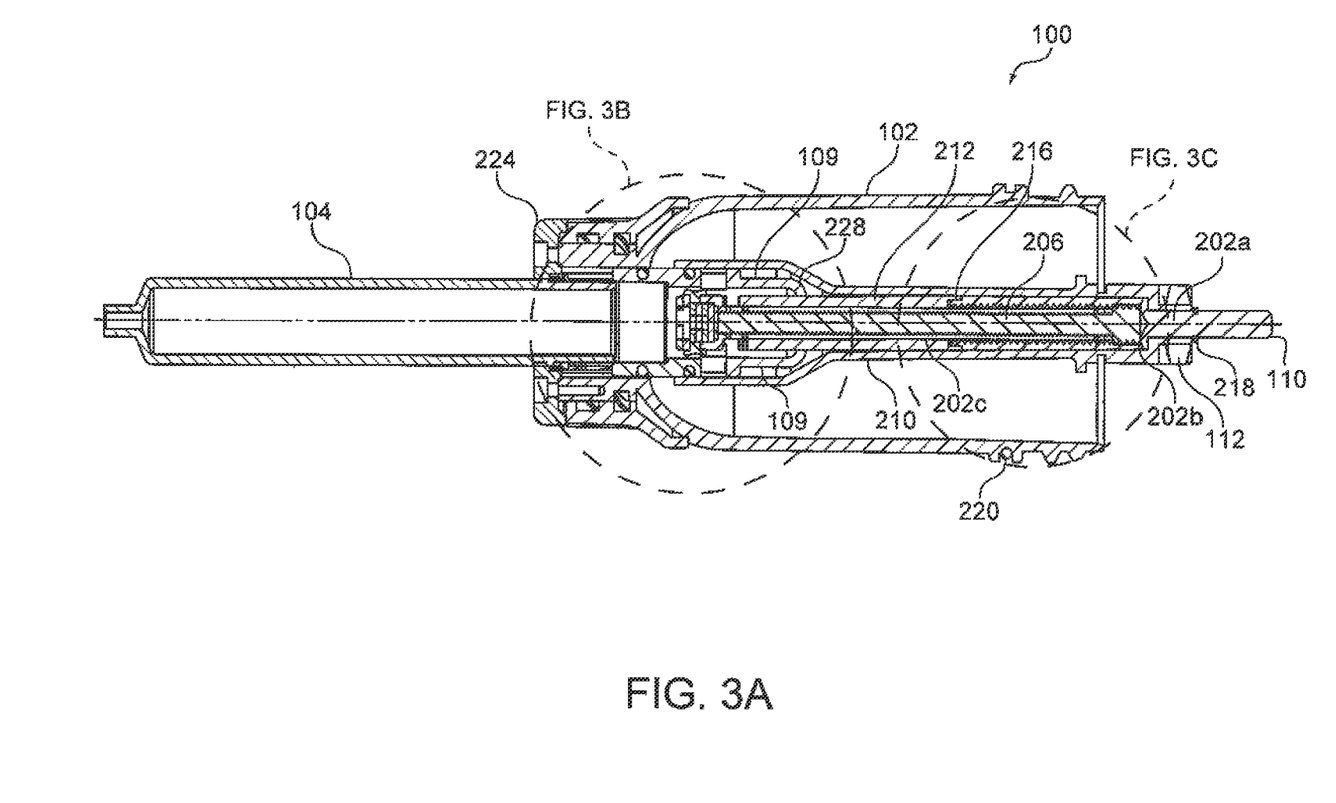
FIGS. 3A to 3C are cross sectional side views of a bone filler mixing and delivery device.
Figure 3B:
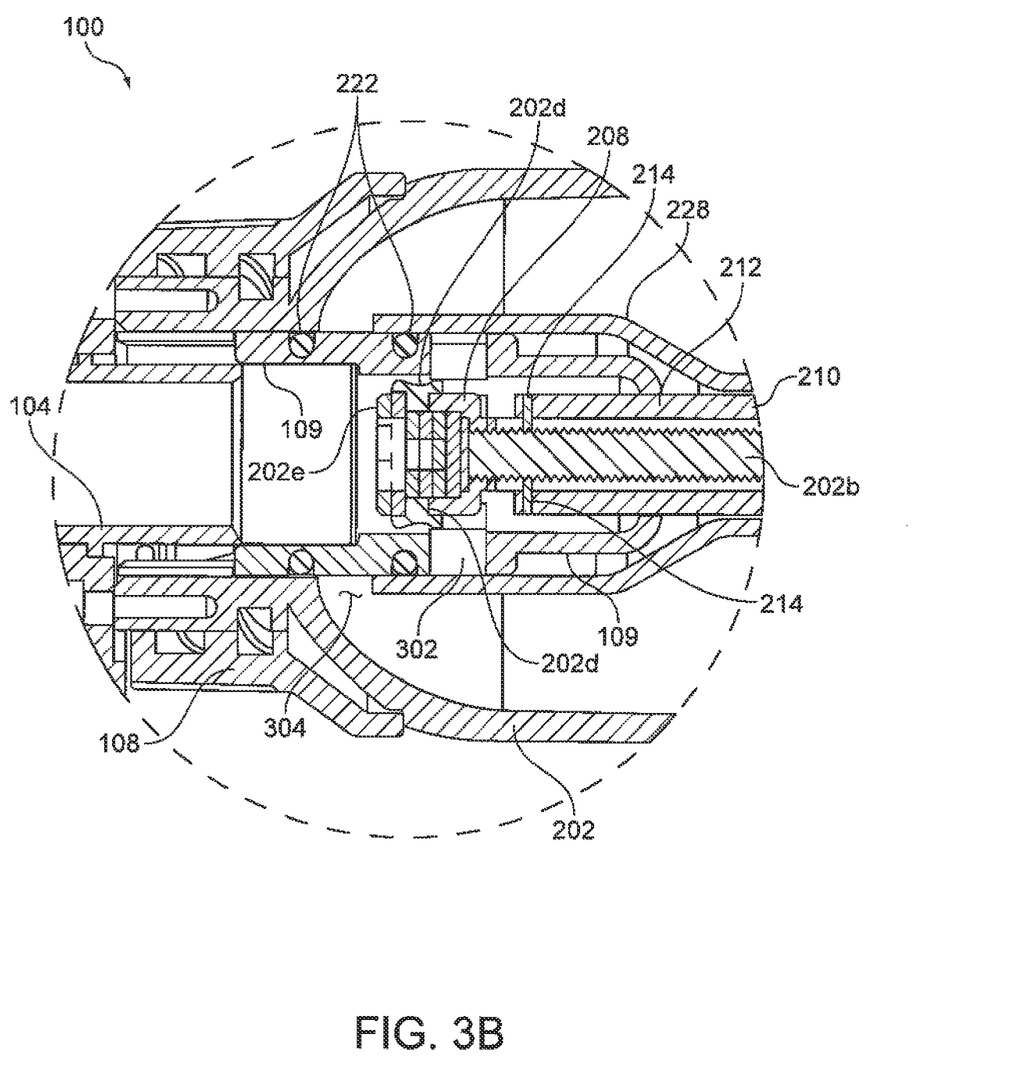
Figure 3C:
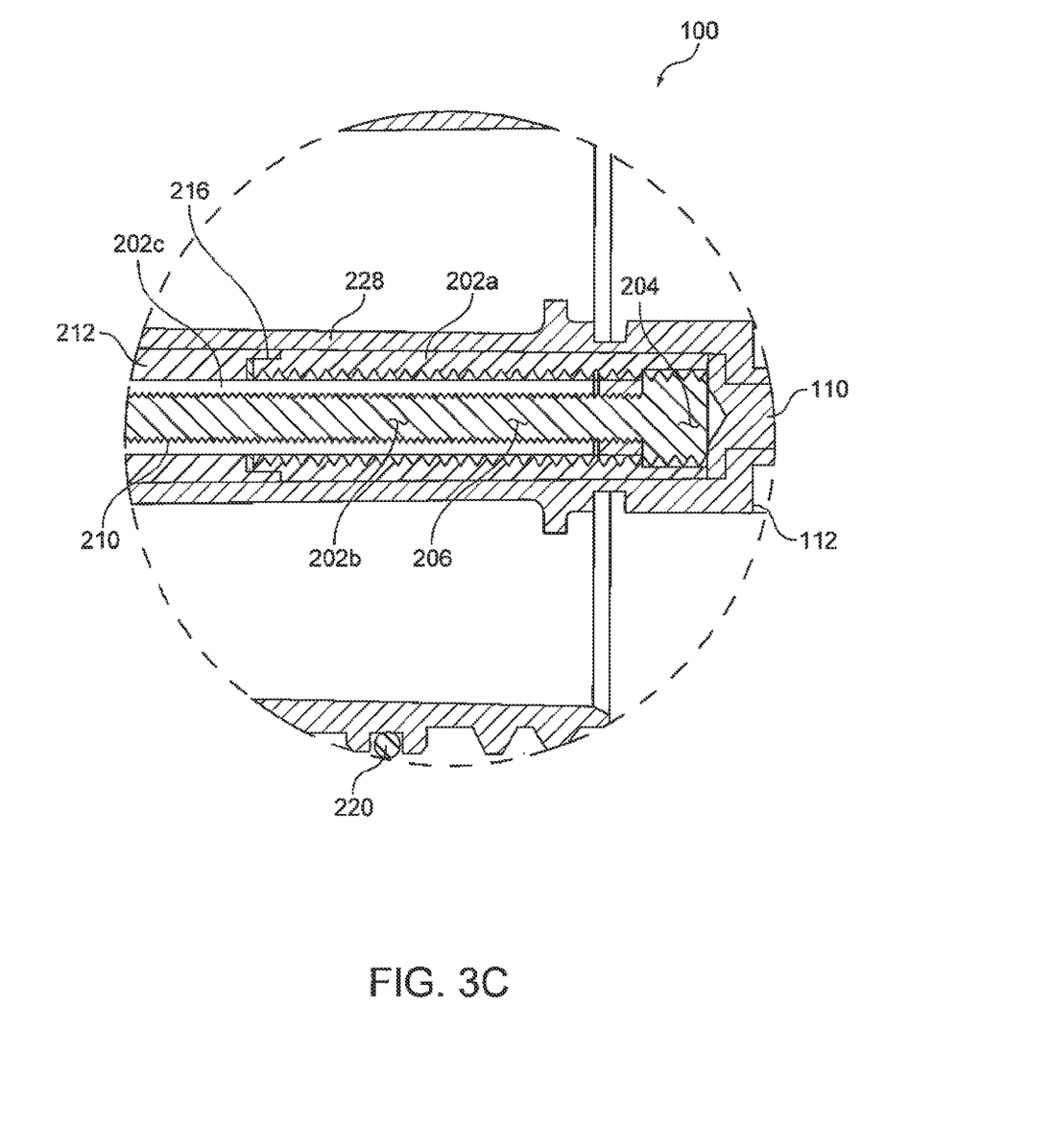

A portion 110 of the drive shaft 202 *a* is adapted to be coupled selectively to a corresponding gripping feature in the crank handle 118. The drive shaft 202 *a* also includes an opening (not visible in FIG. 2, but shown as 502 in FIG. 5B) that extends axially from a forward end of the drive shaft 202 *a*. That opening has internal threads that can engage a corresponding set of threads at on the lead screw 202 *b*. The forward end 232 of the drive shaft 202 *a* has an cuter diameter that is turned down to facilitate engagement with a support sleeve 212 for the plunger shaft 202 *c*. Such engagement may help provide support for the support sleeve 212 when the telescoping plunger assembly is in a retracted position, such as shown in FIGS. 3A-3C.

The lead screw 202 *b* has a wide portion 204 and a narrow portion 206, both of which have external threads. The threads on the wide portion 204 of the lead screw 202 *b* are adapted to engage a corresponding set of internal threads on the drive shaft 202 *a*. The threads on the narrow portion 206 of the lead screw 202 *b* are adapted to engage corresponding internal threads on the plunger shaft 202 *c*. In some implementations, a multiple lead thread is formed on the narrow portion 206 of the lead screw 202 *b* to maximize the axial distance that the plunger shaft 202 *c* moves with each rotation of the lead screw 202 *b*.

According to the illustrated implementation, a seal retaining screw 202 *e* is adapted to hold the plunger seal 202 *d* in place at a front section 208 of the plunger shaft 202 *c*. The front section 208 of the plunger shaft 202 *c* has an internally threaded opening that extends axially rearward from its front surface. That internally threaded opening is adapted to received and engage the seal retaining screw 202 *e*. The seal retaining screw 202 *e* is adapted to pass partially through an axial opening in the plunger seal 202 *d* and hold the plunger seal 202 *d* in place at the front section 208 of the plunger shaft 202 *c*. The seal retaining screw 202 *e* prevents the seal 202 *d* from slipping off the front of the plunger shaft 202 *c*.

The plunger shaft 202 *c* also includes a rear section 210 that has a smaller outer diameter than its front section 208. The rear section 210 has an opening that extends forward from a rear surface of the plunger shaft 202 *c* in an axial direction. That opening is adapted to receive the narrow portion 206 of the lead shaft 202 *b*. The opening has internal threads that are adapted to engage a corresponding set of external threads on the narrow portion 206 of the lead shaft 202 *b*.

The rear section 210 of the plunger shaft 202 *c* has at least one slot 214 in its outer surface that extends longitudinally along a portion of the length of the rear section 210. In the illustrated implementation, the longitudinal slot 214 extends from just behind the front section 208 of the plunger shaft 202 *c* rearward to a short distance from the opposite end of the rear section 210.

A support sleeve 212 is provided for the plunger shaft 202 *c*. In the illustrated implementation, the support sleeve 212 has an axial opening, through which the rear section 210 of the plunger shaft 202 *c* can pass. The rear section 210 of the plunger shaft 202 *c* is adapted to pass snugly through the support sleeve 212. The support sleeve 212 also is adapted to provide mechanical support to the plunger shaft 202 *c*.

According to the illustrated implementation, the plunger shaft 202 *c* is coupled to the support sleeve 212 in a manner that allows relative motion between the plunger shaft 202 *c* and the support sleeve 212 in an axial direction, but prevents relative motion between the plunger shaft 202 *c* and the support sleeve 212 in a rotational direction.

More specifically, pins 215 are provided that extend through holes in support sleeve 212 radially inward toward the plunger shaft 202 *c* and engage the longitudinal slot 214 formed in the rear section 210 of the plunger shaft 202 *c*. The pins 215 prevent relative motion between the plunger shaft 202 *c* and the support sleeve 212 in a rotational direction. Accordingly, when the lead screw 202 *b*, to which the plunger shaft 202 *c* is threaded, rotates inside the plunger shaft 202 *c*, the plunger shaft 202 *c* is forced to move in an axial direction. When the plunger shaft 202 *c* moves in the axial direction, the pins 215 move along the length of the longitudinal slot 214. When the pins 215 reach the end of the longitudinal slots, any further motion of the plunger shaft 202 *c* in the forward direction, causes the pins 215 to drag the support sleeve 212 in the forward axial direction along with the plunger shaft 202 *c*.

According to the illustrated implementation, the sliding tube 109 is adapted to support the support sleeve 212. More specifically, the support sleeve is adapted to fit closely within an axially opening through the sliding tube 109. The sliding tube 109 is coupled to the housing 102 in such a manner as to permit relative motion between the sliding tube 109 and the housing 102 in an axial direction, but to prevent relative motion between the sliding tube 109 and the housing 102 in a rotational direction. Likewise, support sleeve 212 is coupled to sliding tube 109 to permit axial motion but prevent rotation.

The illustrated bone filler mixing and delivery device 100 also includes a retaining ring 216 adapted to be coupled to a forward end of the drive shaft 202 *a*. When the retaining ring 216 is coupled to the forward end of the drive shaft, it prevents the wide portion 204 of the lead screw 202 *b* from inadvertently screwing out of and becoming disengaged from the drive shaft 202 *a*. More specifically, when the rear end 204 of the lead screw 202 *b* reaches the forward end of the drive shaft 202 *a*, it contacts the retaining ring 216, which prevents the lead screw 202 *b* from moving forward any further.

The illustrated bone filler mixing and delivery device 100 also includes a drive shaft retaining ring 213 that is adapted to be coupled to a rear end of the drive shaft 202 *a*. When the drive shaft 202 *a* is positioned inside the mixing element 228 so that its rear portion 110 is exposed through the rear end of the mixing element, the drive shaft retaining ring 218 prevents the drive shaft 202 *a* from moving axially with respect to the mixing element 228.

An O-ring 220 is provided to seal the mixing section 102 at the interface between the housing 102 and the cover assembly 114.

A flange 224 is provided at one end of the device 100 and can be coupled to the housing 102 with screws 226. In certain implementations, the screws 226 are self-threading screws.

The mixing element 228 is adapted to be positioned substantially inside the housing 102. The mixing element 228 includes mixing paddles 230 and a drive 112 for the mixing paddles 230. The mixing paddles 230 are adapted to mix components in the mixing section 102 to form bone filler. An opening extends axially through the mixing element 228 and has a diameter that is large enough to receive the drive shaft 202 *a*. When assembled, the drive shaft 202 *a* is positioned substantially within the opening in the mixing element 228.

FIGS. 3A-3C are cross sectional views of a bone filler mixing and delivery device 100 that includes a telescoping plunger assembly shown in a retracted position. In the retracted position, the illustrated plunger assembly is substantially contained within the mixing section 102 of the device.

As illustrated, the drive shaft 202 *a* of the plunger assembly includes an internally threaded opening that extends axially rearward from a forward end of the drive shaft 202 *a*. The lead screw 202 *b* has a wide portion 204 and a narrow portion 206. The wide portion 204 of the lead screw 202 *b* is coupled to the internal threads of the axial opening that passes through part of the drive shaft 202 *a*. As illustrated, the lead screw 202 *b* is screwed completely into the drive shaft 202 *a*.

The rear section 210 of the plunger shaft 202 *c* has an opening that extends forward from a rear surface of the plunger shaft 202 *c* in an axial direction. The narrow portion 206 of the lead screw 202 *b* is coupled to the internal threads on the axial opening in the rear section 210 of the plunger shaft 202 *c*. As illustrated, the plunger shaft 202 *c* is completely screwed onto the lead screw 202 *b*.

The rear section 210 of the plunger shaft 202 *c* passes through the support sleeve 212. The support sleeve 212 provides mechanical support to the plunger shaft 202 *c*. Two longitudinal slots (not visible) are formed on opposite sides of the plunger shaft 202 *c*. Pins 215 pass radially inward through the support sleeve 212 and engage the longitudinal slots formed in the outer surface of the plunger shaft 202 *c*. Accordingly, the plunger shaft 202 *c* is permitted to move in an axial direction relative to the support sleeve 212, but is prevented from rotating relative to the support sleeve 212.

The support sleeve 212 passes through and is supported by the sliding tube 109 and by the mixing element 228. The support sleeve 212 includes grooves that extend longitudinally along its outer surface. Those grooves are coupled to corresponding fingers that extend radially inward from the sliding tube 109. Accordingly, the support sleeve 212 is prevented from rotating relative to the sliding tube 109, but is permitted to move axially relative to the sliding tube 109.

The sliding tube 109 is supported by the forward end of the mixing element 228 and by the housing 102. As discussed above, the sliding tube 109 includes at least one opening 302 that can align with corresponding opening(s) 304 in the mixing section 102 of the device 100 to provide a flow path between the mixing section 102 and the syringe barrel 104. As illustrated, those openings are not aligned with each other. However, if the sliding tube 109 were moved forward inside the device 100, the openings would be aligned with each other. The sliding tube is coupled to the housing in a manner that prevents relative rotational motion therebetween. The mixing section 102 of the device 100 is sealed at the sliding tube 109 by o-rings 222.

The support sleeve 212 includes a counterbore that is engaged to the turned down outer diameter on the forward end of the drive shaft 202 *a*. That arrangement may, in some implementations, help provide support to the support sleeve 212 when the telescoping plunger assembly is in a retracted position.

Figure 4A:
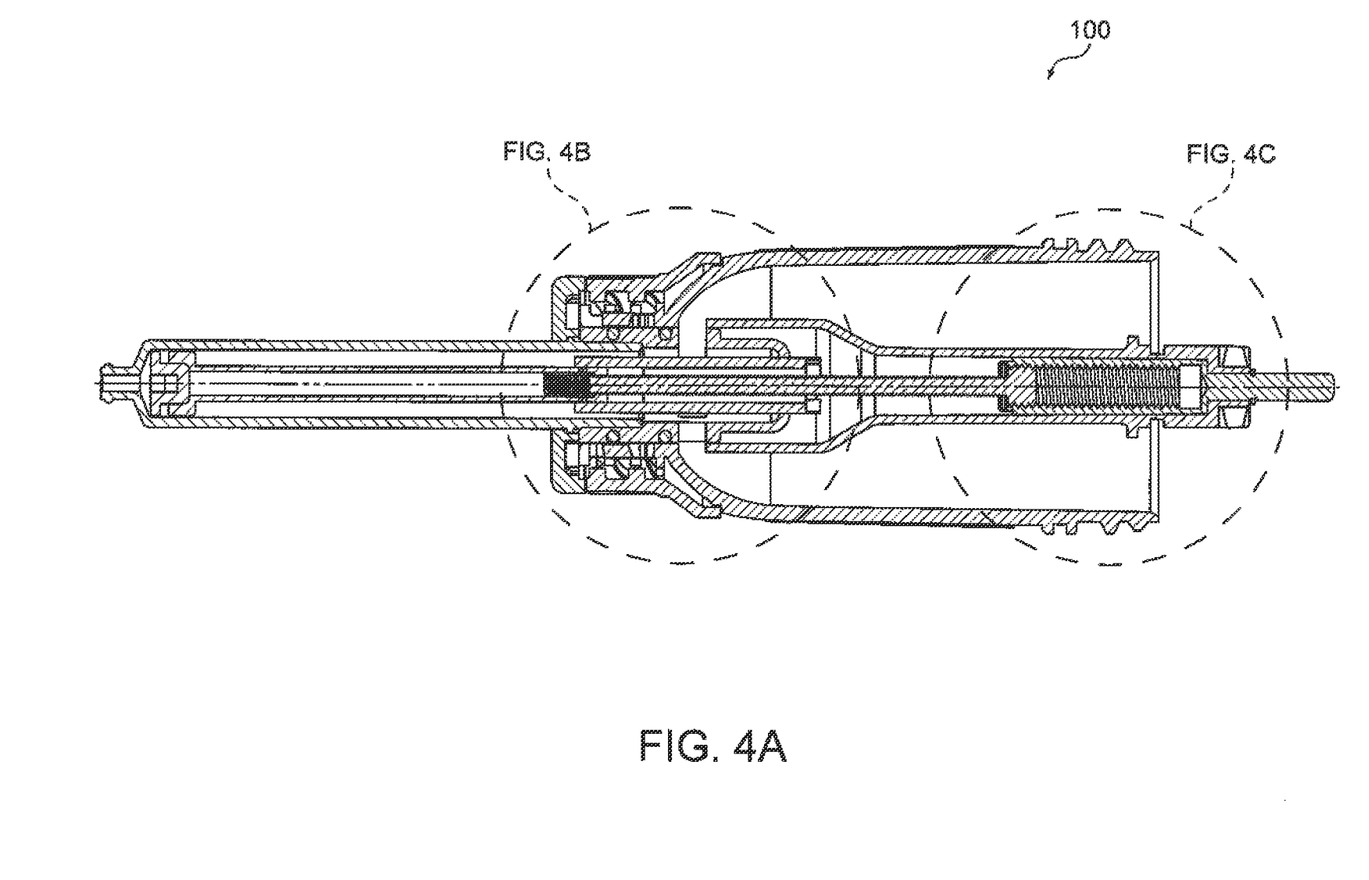
FIGS. 4A to 4C are cross sectional side views of a bone filler mixing and delivery device.
Figure 4B:
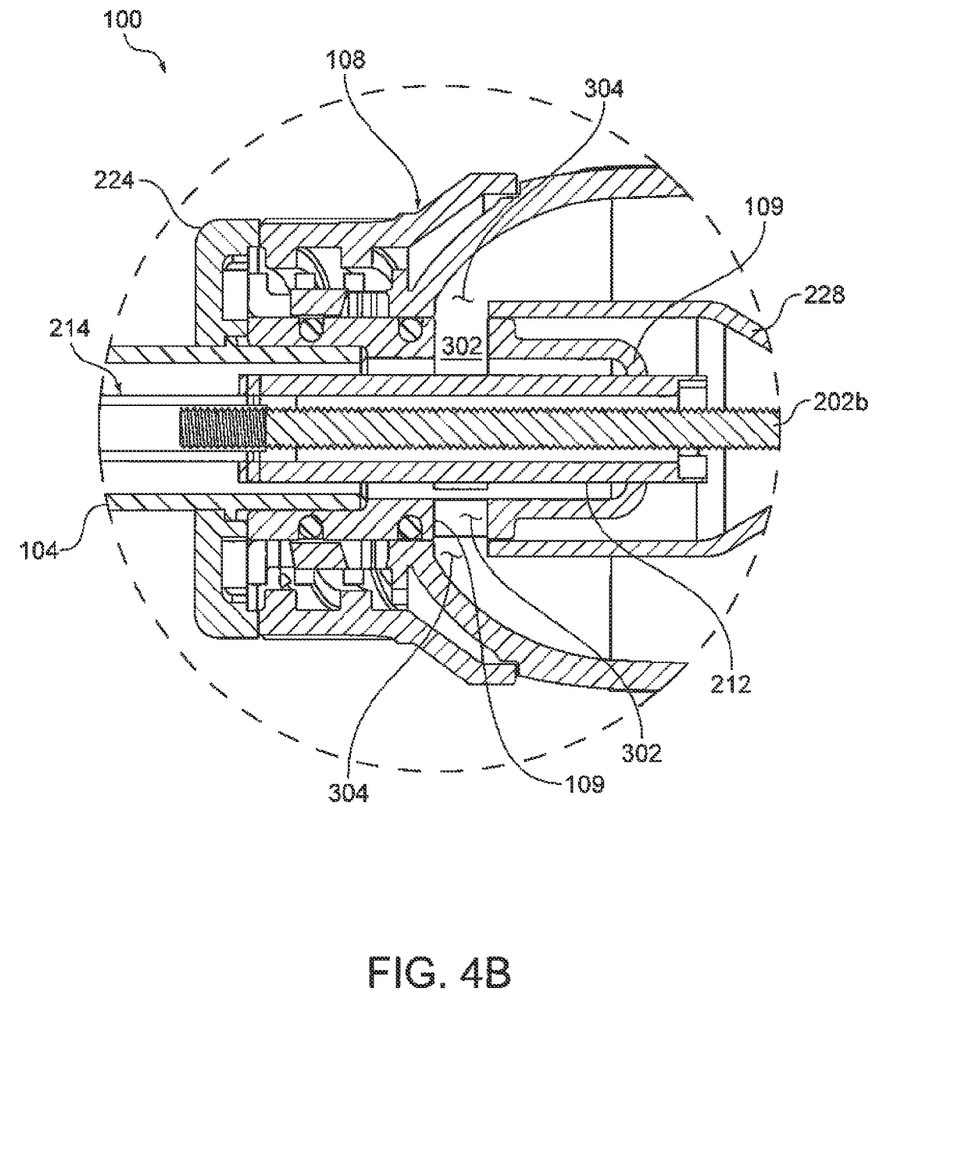
Figure 4C:
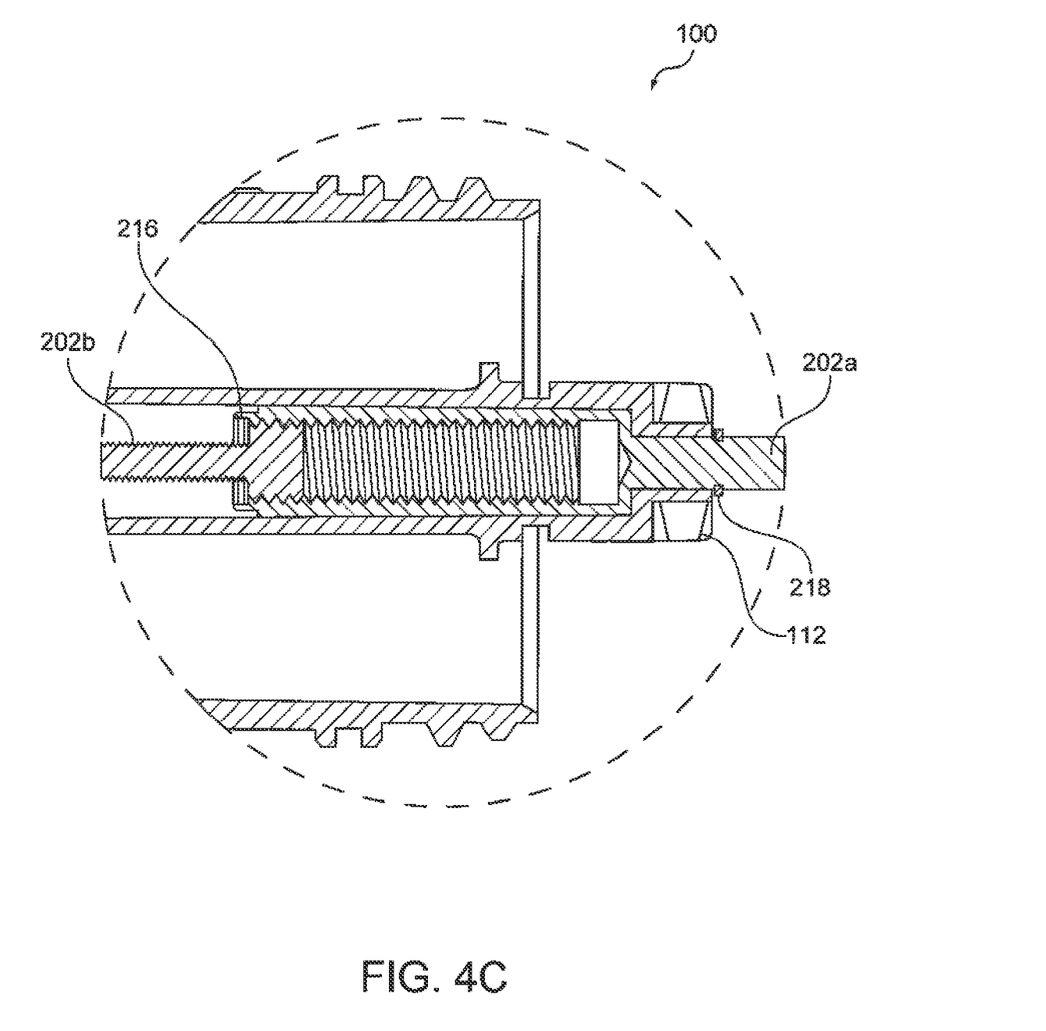

FIGS. 4A-4C are cross sectional views of a bone filler mixing and delivery device 100 that includes a telescoping plunger assembly shown in a fully extended position. In the fully extended position, the illustrated plunger shaft is extended to the forward end of the syringe barrel 104.

As illustrated, the pins 215 are in contact with the rear end of the longitudinal slots 214 formed in the outer surface of the plunger shaft 202 *c*. The sliding tube 212 is shown at a position more forward than its position in FIGS. 3A-3C. The sliding tube 212 in FIGS. 4A-4C has been dragged forward by the pins 215 moving with the plunger shaft 202 *c* beyond the point where the pins 215 came into contact with the rear end of the longitudinal slots 214.

The lead screw 202 *b* is shown as forward as it can be The wide portion 204 of the lead screw 202 *b* is in contact with and prevented from moving forward any further by the retaining ring 216 coupled to the forward end of the drive shaft 202 *a*.

Also, it can be seen that the sliding tube 109 is at a position more forward than it was in FIGS. 3A-3C. In particular, the openings 302 in the sliding tube 109 are aligned with corresponding openings 304 from the mixing section 102.

Figures 5A, 5B, 5C:
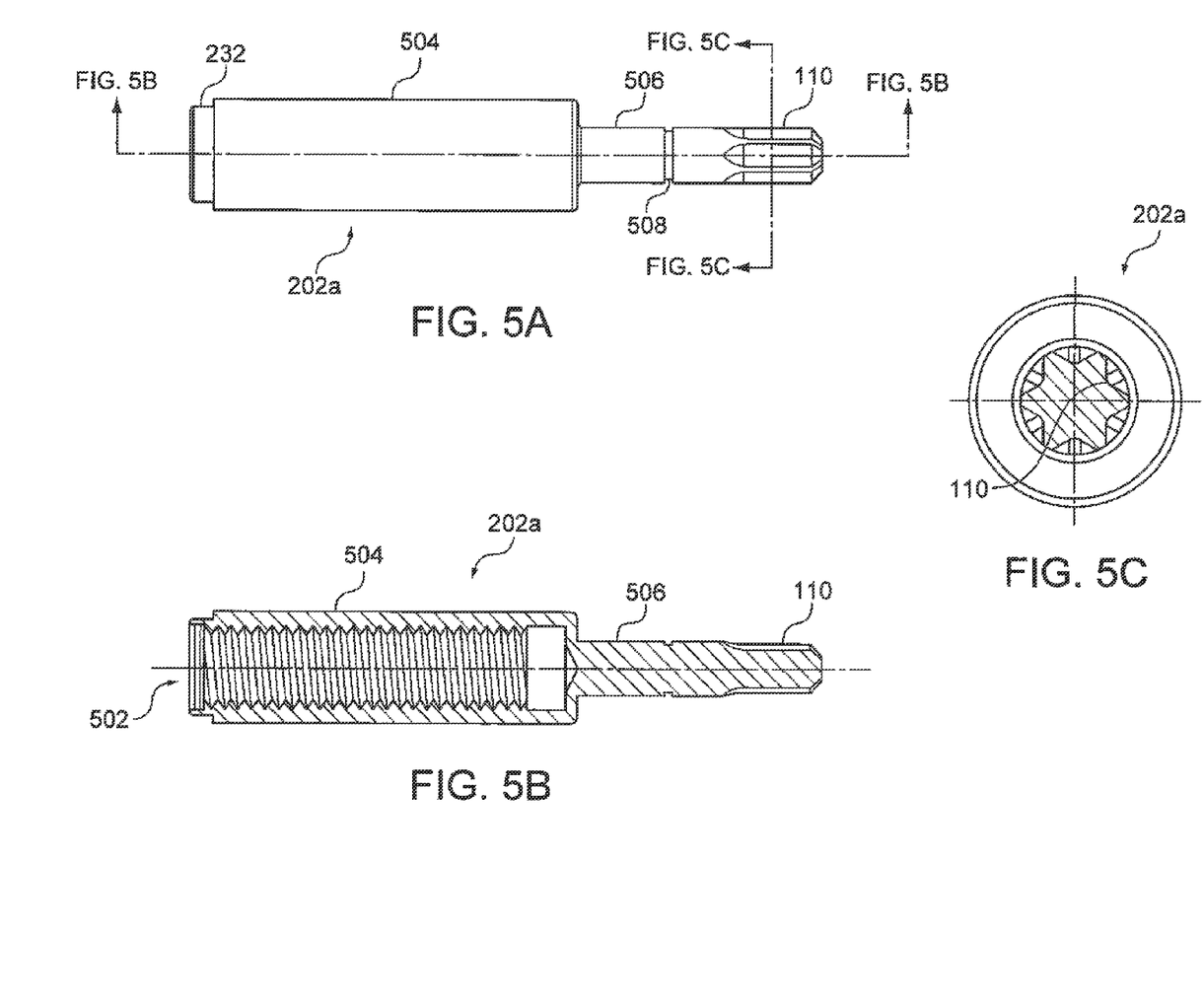
FIGS. 5A to 5C are views of a drive shaft.

FIGS. 5A-5C illustrate a drive shaft 202 *a* for a bone filler mixing and delivery device that includes a telescoping plunger assembly. The illustrated drive shaft 202 *a* has a portion that is adapted to be gripped by a corresponding gripping feature in the crank handle of the device.

The illustrated drive shaft has a wide portion 504 and a narrow portion 506. An opening 502 that extends axially rearward from a forward end of the drive shaft 202 *a* substantially the entire length of the wide portion 504. That opening 502 has internal threads that can engage a corresponding set of threads on a lead screw of the plunger assembly. The end of the narrow portion 506 includes a star configuration that facilitates gripping the drive shaft and rotating it. The narrow portion 506 also includes a radial groove 508 for receiving the retaining ring 218. The forward tip 232 of the drive shaft 202 *a* has an outer diameter that is turned down to facilitate engagement with a support sleeve 212 for the plunger shaft 202 *c*.

Figure 6:
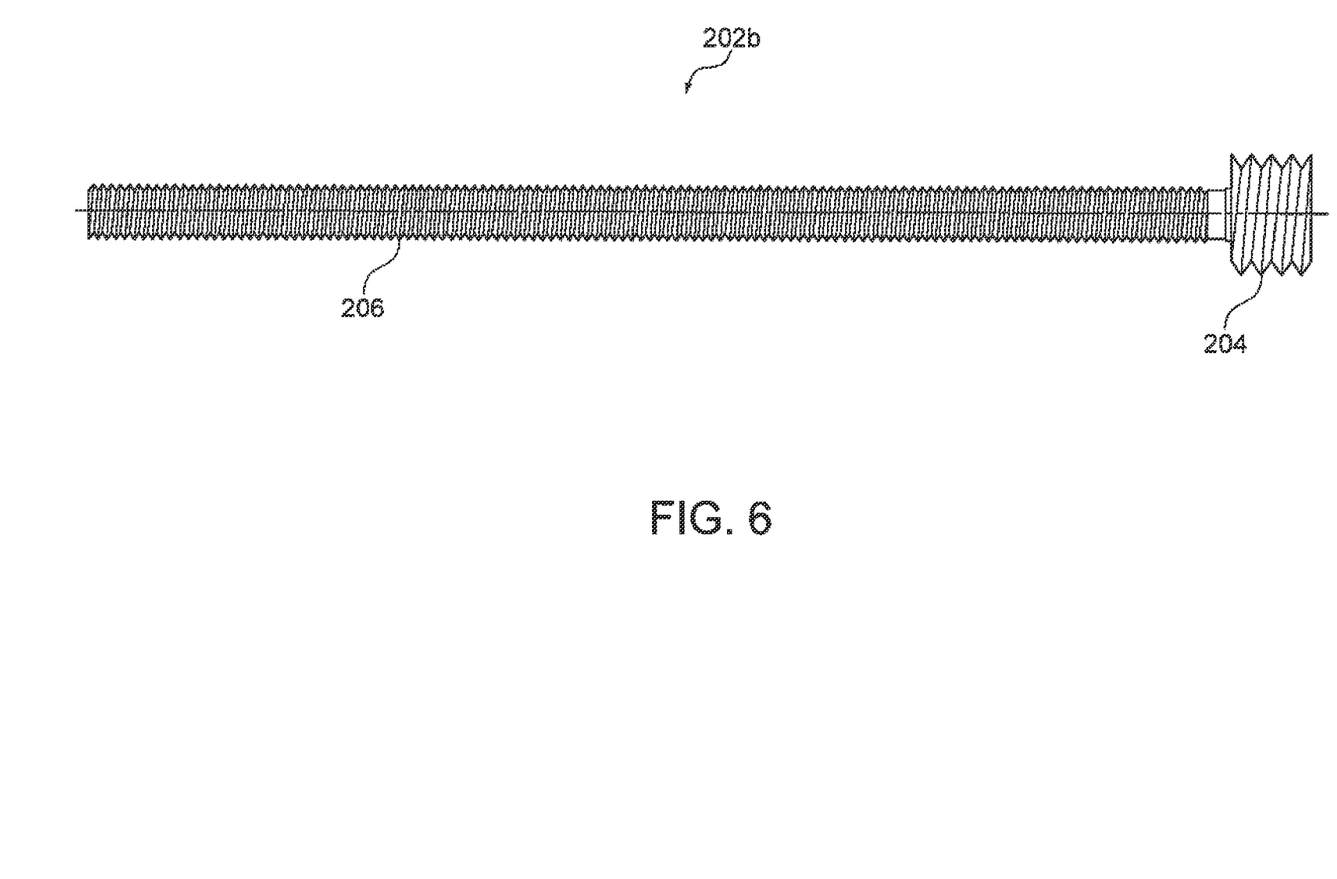
FIG. 6 is a side view of a lead screw.

FIG. 6 is a lead screw 202 *b* for a bone filler mixing and delivery device that includes a telescoping plunger assembly. The illustrated lead screw 202 *b* has a wide portion 204 and a narrow portion 206, both of which have external threads. The threads on the wide portion 204 of the lead screw 202 *b* are adapted to engage a corresponding set of internal threads on a drive shaft for the plunger assembly. The threads on the narrow portion 206 of the lead screw 202 *b* are adapted to engage corresponding internal threads on a plunger shaft of the plunger assembly.

Figure 7A:
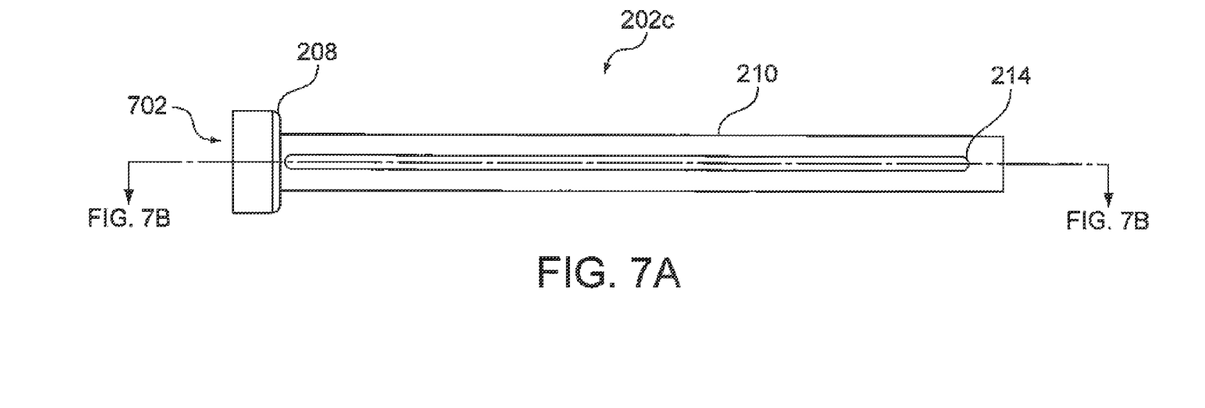
FIGS. 7A and 7B are views of a plunger shaft.
Figure 7B:
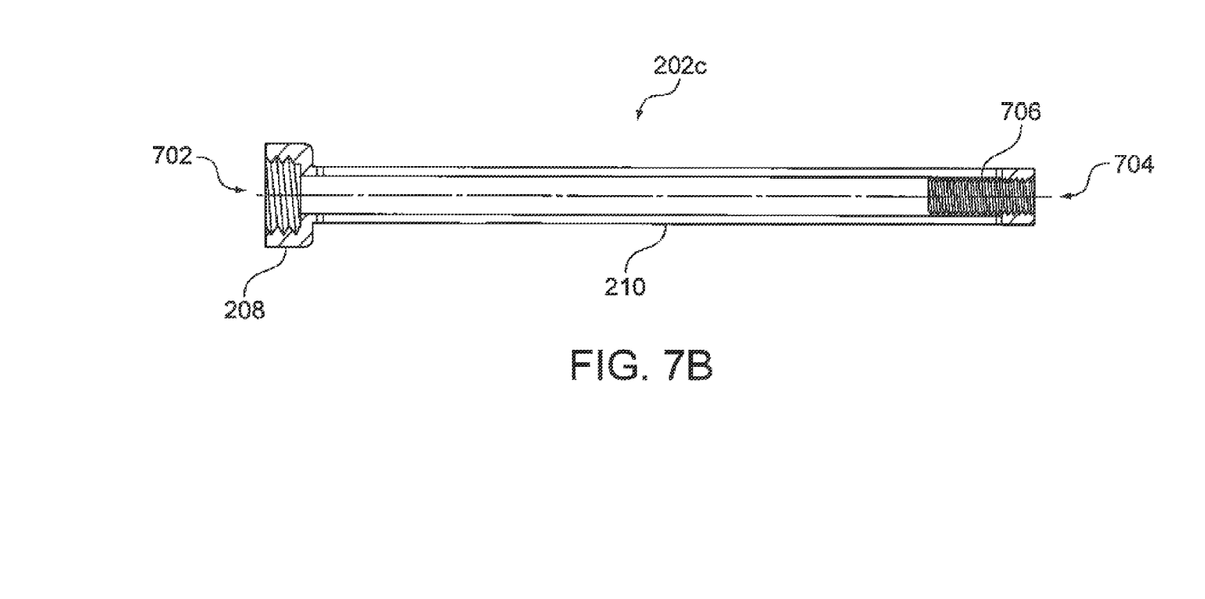

FIGS. 7A and 7B illustrate a plunger shaft 202 *c* for a bone filler mixing and delivery device that includes a telescoping plunger assembly. The illustrated plunger shaft 202 *c* has a rear section 210 that has a smaller outer diameter than its front section 208. The rear section 210 has an opening 704 that extends forward from a rear surface of the plunger shaft 202 *c* in an axial direction. That opening 704 is adapted to receive a lead shaft of the telescoping plunger assembly. That opening 704 has internal threads 706 that are adapted to engage a corresponding set of external threads on a lead shaft of the telescoping plunger assembly.

The rear section 210 of the plunger shaft 202 *c* has a slot 214 in its outer surface that extends longitudinally along a portion of the length of the rear section 210. In the illustrated implementation, the longitudinal slot 214 extends from just behind the front section 208 of the plunger shaft 202 *c* rearward to a short distance from the opposite end of the rear section 210.

The illustrated plunger shaft also has an opening for receiving a seal retaining screw. The opening 702 includes internal threads adapted to engage the threads of the seal retaining screw.

Figure 8A:
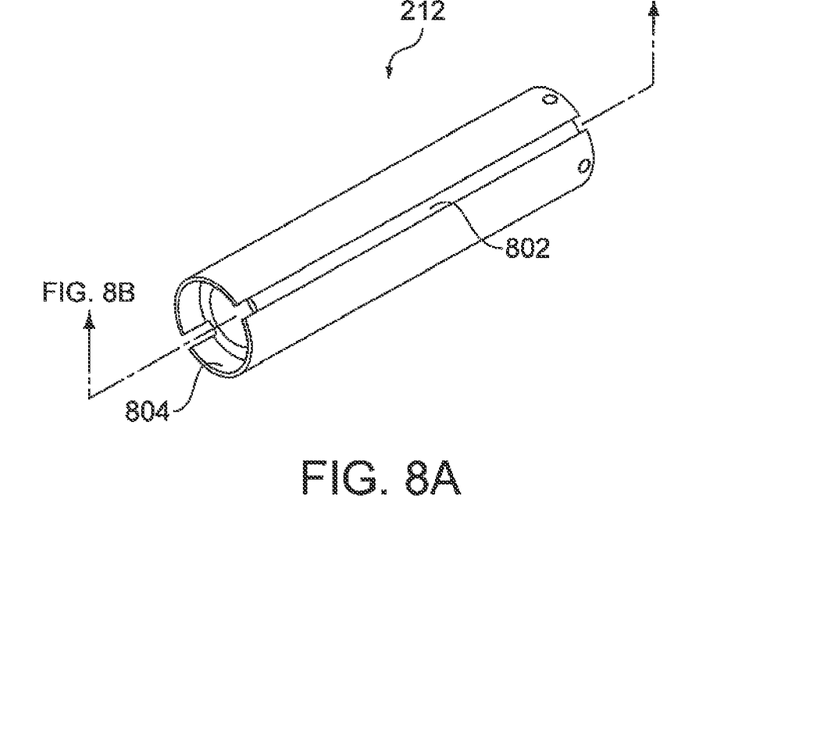
FIGS. 8A and 8B are views of a support sleeve.
Figure 8B:
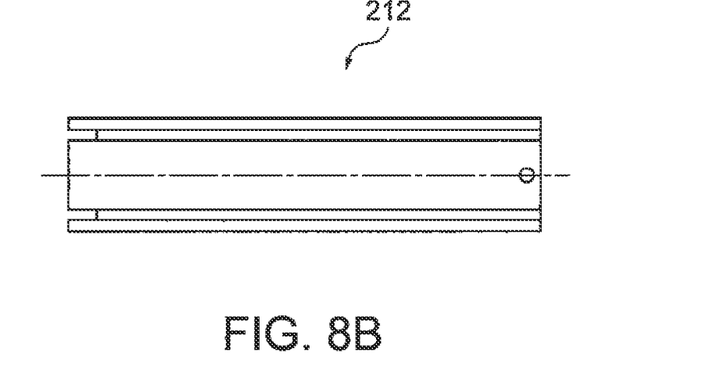

FIGS. 8A and 8B illustrate a support sleeve 212 that can be used to support a plunger shaft in a bone filler mixing and delivery device with a telescoping plunger assembly. The illustrated support sleeve 212 has an axial opening 804 adapted to engage the turned down portion 232 of the drive shaft 202 *a* of the telescoping plunger assembly.

The illustrated support sleeve 212 includes grooves 802 that extend lengthwise down its outer surface. Those grooves 802 are adapted to engage corresponding fingers or pins of the sliding tube which prevent the support sleeve from rotating. The illustrated support sleeve also includes holes that are adapted to receive pins with which to engage corresponding slots formed in the outer surface of a plunger shaft inside the support sleeve 212.

Various modifications of the techniques and structures described herein are possible. For example, although the above discussion is directed primarily to a bone filler mixing and delivery device, a person of ordinary skill in the art would recognize that the techniques and structures disclosed could be applied beneficially to any device that mixes and delivers fluids other than bone filler.

Additionally, the techniques and structures described above could be readily incorporated into a fluid delivery device that does not include a mixing section. Such a device may simply include a temporary storage compartment (without a mixing element) coupled to a syringe barrel. In those instances, the telescoping plunger assembly may be adapted to retract to a compact state substantially contained within the temporary storage compartment. When a user is ready to deliver the fluid, the user might transfer a desired amount of fluid into the syringe barrel and then deploy the telescoping plunger to extend from the temporary storage compartment through the syringe barrel.

Moreover, various different arrangements may be utilized to restrict relative motion between parts in one manner, but to permit relative motion in another manner. For example, in some implementations, mating internal and external hexagonal (or other shaped) surfaces may be provided.

Additionally, other methods could be implemented to restrict relative motion between the various components discussed above. For example, the plunger shaft could have an outer surface that is shaped like a hexagon and the support sleeve, within which the plunger shaft sits, could have an axial passage that is shaped like a hexagon as well. In such an implementation, when the plunger shaft positioned inside the passage, the plunger shaft would be allowed to move axially relative to the support sleeve, but its relative rotational freedom would be restricted.

Also, the controllable portal that is provided to enable a user to open a flow path between the mixing section and the syringe barrel can be any arrangement that is suitable to perform such a function. For example, the controllable portal may be adapted for actuation by rotating an actuator, by sliding an actuator, by squeezing an actuator or by performing any other motion. The controllable portal may include two openings that can be aligned with each other to establish the flow path. Alternatively, the controllable portal may include a frangible seal, where the frangible seal can be ruptured to establish the flow path. The controllable portal can include any type of valve assembly. A person of ordinary skill would recognize a number of different ways of implementing the controllable portal disclosed herein.

Additionally, it is possible to couple the various elements of the plunger assembly to each other using various combinations of internal/external threading. A person of ordinary skill in the art would recognize that the particular examples disclosed herein are illustrative only and the scope of the claims should not be restricted merely to the particular arrangements disclosed.

Moreover, although the plunger assembly disclosed herein is adapted to extend or retract in response to a user rotating the crank handle, a person of ordinary skill in the art would recognize that other methods of moving the plunger assembly may be implemented. For example, a ratcheting mechanism could be provided, the manipulation of which causes the telescoping plunger to extend or retract.

Various other modifications of the methods and structures disclosed herein are possible. Accordingly, other implementations are within the scope of the following claims.

What is claimed is:

1. A method of delivering a bone filler with a mixing and delivery device, the mixing and delivery device comprising:
    a mixing section;
    a syringe barrel coupled to the mixing section;
    a controllable portal between the mixing section and the syringe barrel;
    a plunger assembly comprising a plunger shaft having a longitudinal slot and a support sleeve positioned over the plunger shaft;
    a pin member extending radially through at least one hole in the support sleeve toward the plunger shaft and engaging the longitudinal slot, wherein when the plunger shaft moves in a first direction, the pin member translates along the longitudinal slot and drags the support sleeve in the same direction, and wherein the pin member is in contact with a rear end of the longitudinal slot formed in the outer surface of the plunger shaft,
    wherein the pin member that extends from the support sleeve to engage the longitudinal slot prevents the plunger shaft from rotating about the axis,
    the method comprising:
    mixing one or more components in the mixing section to form a bone filler;
    opening the controllable portal to allow the bone filler to flow from the mixing section to the syringe barrel; and
    dispensing the bone filler from an opening in the syringe barrel by extending the plunger assembly telescopically in an axial direction through the syringe barrel.

2. The method of claim 1, further comprising retracting the plunger assembly telescopically to a position completely contained within the mixing section.

3. The method of claim 1, wherein the plunger assembly further comprises:
    a drive shaft that can be rotated about an axis;
    a lead screw threaded to the drive shaft; and
    wherein the plunger shaft is threaded to the lead screw.

4. The method of claim 3, wherein the drive shaft is restricted from moving in an axial direction, and wherein the plunger shaft is restricted from moving in a rotational direction.

5. The method of claim 3, further comprising a cover assembly with a manually actuable crank handle, that is movable to a first position to engage a mixing element in the mixing section and disengage the drive shaft, movable to a second position to engage the drive shaft and disengage the mixing element, and movable to drive the engaged mixing element or the engaged drive shaft.

6. The method of claim 3, further comprising rotating the drive shaft to cause relative rotation between the lead screw and at least one of either the plunger shaft or the drive shaft.

7. The method of claim 6, wherein the relative rotation causes the plunger shaft to move axially through the bone filler mixing and delivery device.

8. The method of claim 3, wherein the lead screw comprises:
a first portion threaded to the drive shaft; and
a second portion threaded to the plunger shaft.

9. The method of claim 3, further comprising a retaining ring coupled to a forward end of the drive shaft, wherein the retaining ring is adapted to engage the lead screw when the lead screw nears an end of its stroke, and wherein engagement between the retaining ring and the lead screw prevents the lead screw from becoming disengaged from the drive shaft.

10. The method of claim 1, wherein the plunger shaft is coupled to the support sleeve to allow relative motion between the plunger shaft and the support sleeve in an axial direction, but to restrict relative motion between the plunger shaft and the support sleeve in a rotational direction.

11. The method of claim 1, wherein the support sleeve is movable in an axial direction and wherein the pin member is adapted to drag the sleeve in the axial direction with the plunger shaft as the plunger shaft moves beyond an axial position where the pin reaches an end of the longitudinal slot.

12. The method of claim 1, wherein the support sleeve is coupled to a sliding tube to permit relative motion between the sliding tube and the support sleeve in an axial direction but to prevent relative motion between the sliding tube and the support sleeve in a rotational direction.

13. The method of claim 1, wherein the bone filler comprises a bone cement.

14. A method of delivering a material with a material delivery device, the material delivery device comprising:
a syringe barrel;
an access portal;
a plunger assembly comprising a plunger shaft comprising a longitudinal slot and a support sleeve positioned over the plunger shaft; and
a pin member that extends radially through at least one hole in the support sleeve toward the plunger shaft and engages the longitudinal slot, wherein when the plunger shaft moves in a first direction, the pin member translates along the longitudinal slot and drags the support sleeve in the same direction, and wherein the pin member is in contact with a rear end of the longitudinal slot formed in the outer surface of the plunger shaft,
wherein the pin member that extends from the support sleeve to engage the longitudinal slot prevents the plunger shaft from rotating about the axis,
the method comprising:
loading material into the syringe barrel through the access portal; and
dispensing the material from an opening in the syringe barrel by extending the plunger assembly telescopically in an axial direction through the syringe barrel.

15. The method of claim 14, further comprising retracting the plunger assembly telescopically to a position completely withdrawn from the syringe barrel.

16. The method of claim 14, wherein the plunger assembly further comprises:
a drive shaft that can be rotated about an axis;
a lead screw threaded to the drive shaft; and
wherein the plunger shaft is threaded to the lead screw.

17. The method of claim 16, wherein the drive shaft is restricted from moving in an axial direction, and wherein the plunger shaft is restricted from moving in a rotational direction.

18. The method of claim 14, wherein the support sleeve is adapted to provide mechanical support to the plunger shaft, and wherein the plunger shaft is coupled to the support sleeve in a manner that allows relative motion between the plunger shaft and the support sleeve in an axial direction, but restricts relative motion between the plunger shaft and the support sleeve in a rotational direction.

19. The method of claim 14, wherein the support sleeve is movable in an axial direction and wherein the pin member is adapted to drag the sleeve in the axial direction with the plunger shaft as the plunger shaft moves beyond an axial position where the pin member reaches an end of the longitudinal slot.

* * * * *